United States Patent
Kimoto

(10) Patent No.: US 7,492,320 B2
(45) Date of Patent: Feb. 17, 2009

(54) ANTENNA UNIT AND METHOD FOR MANUFACTURING ANTENNA UNIT

(75) Inventor: Seiichiro Kimoto, Hachioji (JP)

(73) Assignee: Olympus Corporation, Tokyo (JP)

( * ) Notice: Subject to any disclaimer, the term of this patent is extended or adjusted under 35 U.S.C. 154(b) by 96 days.

(21) Appl. No.: 11/630,806

(22) PCT Filed: Aug. 31, 2005

(86) PCT No.: PCT/JP2005/015929

§ 371 (c)(1),
(2), (4) Date: Dec. 27, 2006

(87) PCT Pub. No.: WO2006/025457

PCT Pub. Date: Mar. 9, 2006

(65) Prior Publication Data

US 2007/0241975 A1    Oct. 18, 2007

(30) Foreign Application Priority Data

Sep. 1, 2004   (JP) ............................ 2004-254727

(51) Int. Cl.
*H01Q 1/12* (2006.01)
*A61B 5/05* (2006.01)

(52) U.S. Cl. ........................... 343/718; 600/424

(58) Field of Classification Search ........... 343/718, 343/830, 866; 600/410, 424
See application file for complete search history.

(56) References Cited

U.S. PATENT DOCUMENTS

| | | | | |
|---|---|---|---|---|
| 5,604,531 A | | 2/1997 | Iddan et al. | 348/76 |
| 6,592,579 B2 * | | 7/2003 | Arndt et al. | 606/32 |
| 6,904,308 B2 | | 6/2005 | Frisch et al. | 600/424 |
| 6,918,872 B2 * | | 7/2005 | Yokoi et al. | 600/129 |
| 2001/0035902 A1 | | 11/2001 | Iddan et al. | |

FOREIGN PATENT DOCUMENTS

| | | |
|---|---|---|
| JP | 2001-198096 A | 7/2001 |
| JP | 2002-248081 A | 9/2002 |
| JP | 2003-19111 | 1/2003 |
| JP | 2003-210395 A | 7/2003 |
| KR | 10-2003-0084017 A | 11/2003 |
| WO | WO03/001966 A2 | 1/2003 |

* cited by examiner

*Primary Examiner*—Shih-Chao Chen
(74) *Attorney, Agent, or Firm*—Scully, Scott, Murphy & Presser, P.C.

(57) ABSTRACT

A coaxial cable A12 of a receiving antenna A1, a resin plate A13, and a connecting unit cover A15 are fused by thermal treatment, so that a gap between the outer coating of the coaxial cable A12 and the connecting unit cover A15, and a gap between the resin plate A13 and the connecting unit cover A15 are eliminated, whereby they are integrally configured. An antenna of the antenna unit, a coaxial cable, and a connecting unit cover are fused for coverage, and thereby it becomes possible to improve drip-proofness of the antenna unit by preventing water from entering from the gap between these materials when disinfectant is sprayed by misting, for example.

8 Claims, 7 Drawing Sheets

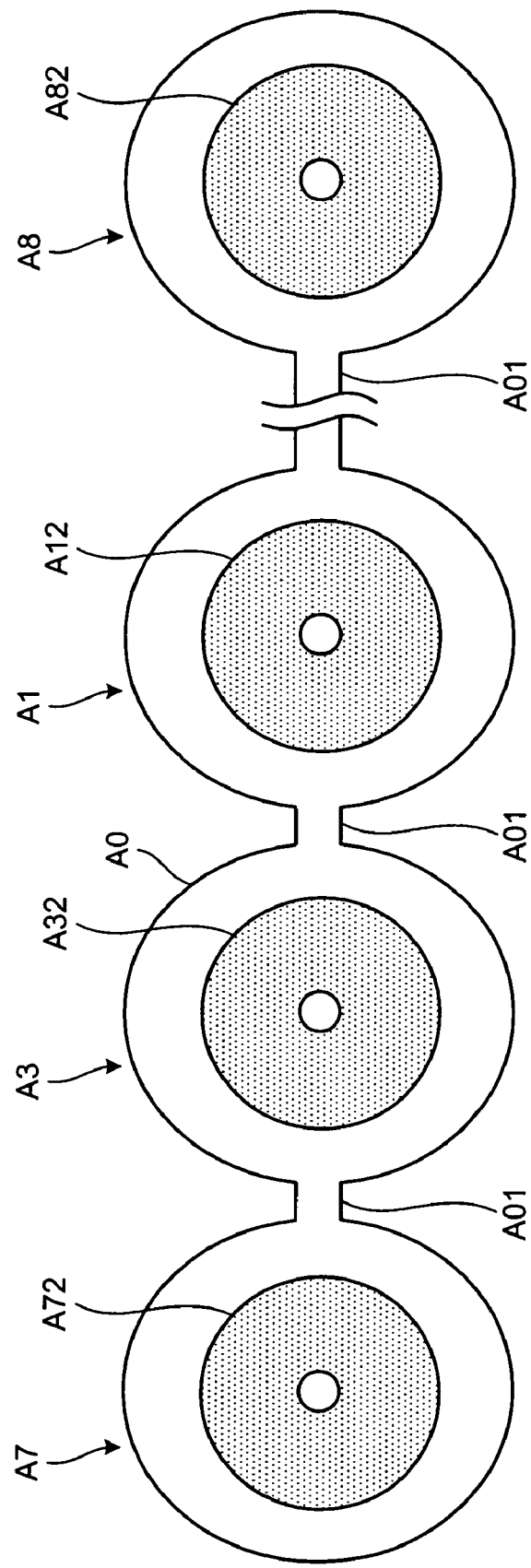

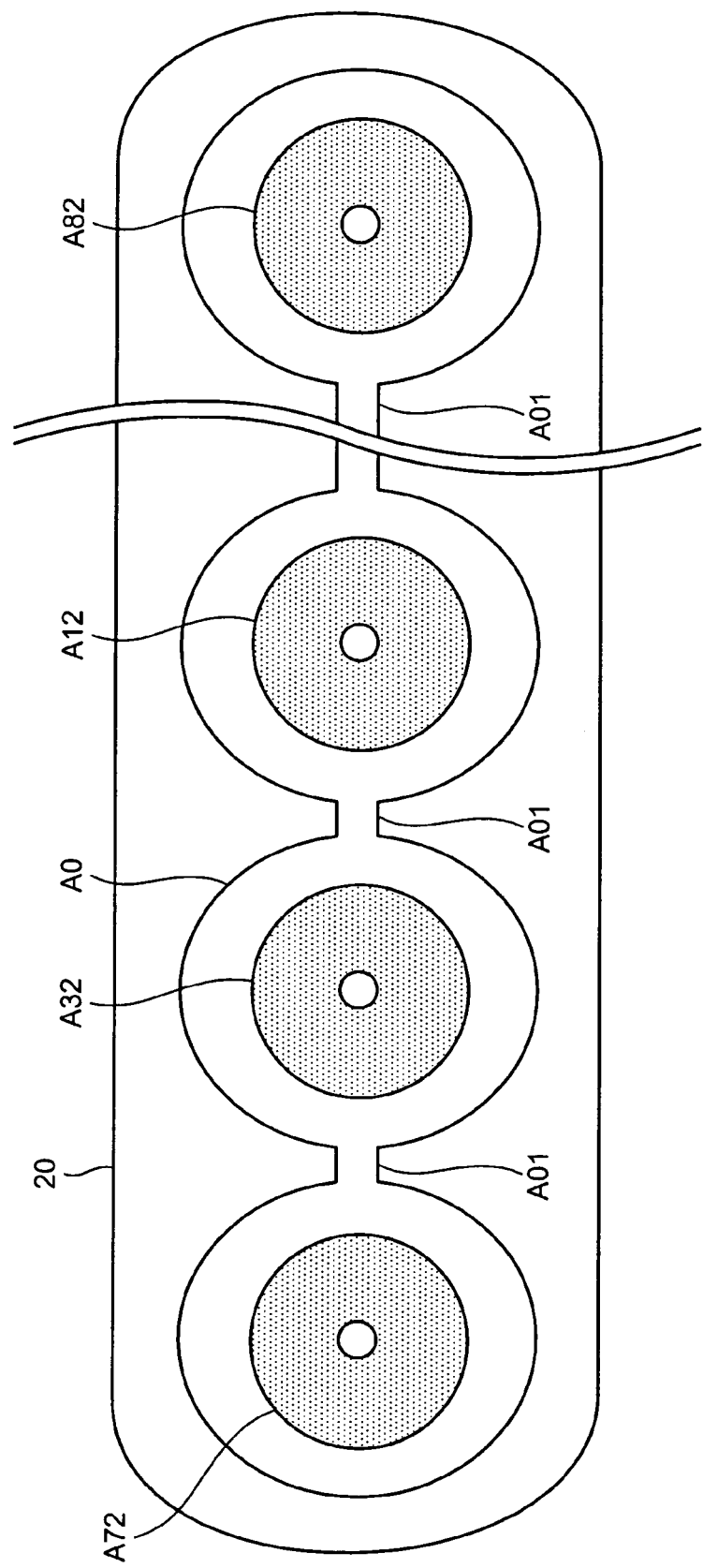

ANTENNA UNIT AND METHOD FOR MANUFACTURING ANTENNA UNIT

TECHNICAL FIELD

The present invention relates to an antenna unit having an antenna and a coaxial cable that connects a receiving device. More specifically, the present invention relates to an antenna unit for laying an antenna on a body of an examinee, and a method for manufacturing the antenna unit.

BACKGROUND ART

Recently, in the field of endoscopes, a capsule endoscope equipped with an imaging function and a radio communication function emerges. The capsule endoscope is swallowed from a mouth of an examinee, which is a subject (human body), for observation (examination) and is naturally discharged from the organism of the subject later. During this observation period, the capsule endoscope moves through the inside of internal organs (the inside of a body cavity) such as a stomach, and a small intestine following the peristaltic activity of the organs, and sequentially images the internal organs using its imaging function.

In the observation period during which the capsule endoscope moves through the internal organs, image data imaged in the body cavity by the capsule endoscope is sequentially transmitted to outside the subject by a radio communication function such as Bluetooth. The image data is accumulated in a memory provided in an external receiving device. The examinee carries the receiving device having a radio communication function and a memory function so as to freely move without experiencing any inconvenience even in the observation period after swallowing the capsule endoscope until naturally discharging the same. After the observation, a doctor or a nurse displays the image imaged in the body cavity on a display unit such as a display to perform a diagnosis based on the image data accumulated in the memory of the receiving device.

Generally, the receiving device includes a plurality of antenna elements that receive an image signal transmitted from the capsule endoscope, and the plurality of antenna elements are dispersedly arranged on the exterior of the subject. The receiving device switches and selects an antenna element with few reception errors of the image signal for reception of the image signal. Patent Document 1 describes a receiver in which antenna elements each having an adhesive adhere to a predetermined region on the subject so that the antenna elements are arranged on the exterior of the subject, and receptions of the plurality of antennas are switched, whereby a location of an in-vivo capsule endoscope, which is a transmission source of an image signal, is detected based on an electric-field strength received by each antenna element. Generally, the antenna element includes an antenna main body, and a coaxial cable that adheres to the antenna main body so as to be electrically connected thereto.

Patent Document 1: Japanese Patent Application Laid-open No. 2003-19111

DISCLOSURE OF INVENTION

Problem to be Solved by the Invention

However, since the antenna element is a medical appliance, the antenna element needs to be sterilized before its use. The sterilization is performed by misting, that is, spraying disinfectant to the antenna element, for example. Because of the misting, water may penetrate into the antenna element from a connecting unit between a cable and an antenna, and, in the conventional antenna element, it is not possible to sufficiently secure drip-proofness.

The present invention has been achieved in view of the above problems, and an object of the invention is to provide an antenna unit and a method for manufacturing the antenna unit, capable of preventing water from penetrating into a gap that exists at a connecting unit between the antenna of the antenna unit and a coaxial cable, whereby drip-proofness is improved.

Means for Solving Problem

An antenna unit according to one aspect of the present invention includes: an antenna attached to a body of an examinee; a coaxial cable that can transmit a signal received by the antenna to a receiving device; a connecting unit cover that covers an electrical connecting unit between the antenna and the coaxial cable, wherein a fusing point of an outermost layer of the coaxial cable and a fusing point of the connecting unit cover are made approximately the same, and the coaxial cable and the connecting unit cover are fused.

In the antenna unit, the outermost layer of the coaxial cable and the connecting unit cover may have compatibility at the time of fusing the outermost layer of the coaxial cable and the connecting unit cover.

In the antenna unit, the outermost layer of the coaxial cable and the connecting unit cover may be formed of the same material.

In the antenna unit, the antenna may include: an antenna main body; and an antenna coating member that envelopes the antenna main body into an interior of the antenna coating member, wherein the antenna coating member may be formed of a material having compatibility with the connecting unit cover at the time of fusing the antenna coating member with the connecting unit cover.

In the antenna unit the coaxial cable may be formed such that the outermost layer covers an intermediate coating layer formed of polyethylene.

In the antenna unit, the electrical connecting unit may be formed such that the outermost layer of the coaxial cable and a coaxial axis exposed from the intermediate coating layer are connected to the antenna.

In the antenna unit, the coaxial cable may enter into an interior of the receiving device so that the coaxial cable and the receiving device are connected, and the outermost layer may be provided such that the outermost layer advances at least to the interior of the receiving device.

A method for manufacturing an antenna unit according to another aspect of the present invention includes: fitting a coaxial cable and an antenna electrically connected into a mold; charging into the mold a liquefied material that configures a connecting unit cover that covers an electrical connecting unit between the antenna and the coaxial cable so that an outermost layer of the coaxial cable melts and the liquefied material that configures the connecting unit cover is compatible with a material that configures the outermost layer; and connecting the connecting unit cover to the coaxial cable after cooling.

Effect of the Invention

In the antenna unit according to the present invention, the fusing point of a coaxial cable that can transmit the signal received by the antenna to the receiving device, and the fusing point of a connecting unit cover that covers an electrical connecting unit between the antenna and the coaxial cable are rendered approximately the same. The coaxial cable and the connecting unit cover are fused in this state. It becomes thereby possible to prevent water from penetrating into a gap that exists between the connecting unit cover and the coaxial cable, and improve the drip-proofness.

BRIEF DESCRIPTION OF DRAWINGS

FIG. 6 is a cross-sectional view taken along the line B-B in FIG. 5; and

FIG. 7 is a cross-sectional view taken along the line C-C in FIG. 5

EXPLANATIONS OF LETTERS OR NUMERALS

Figure 1:
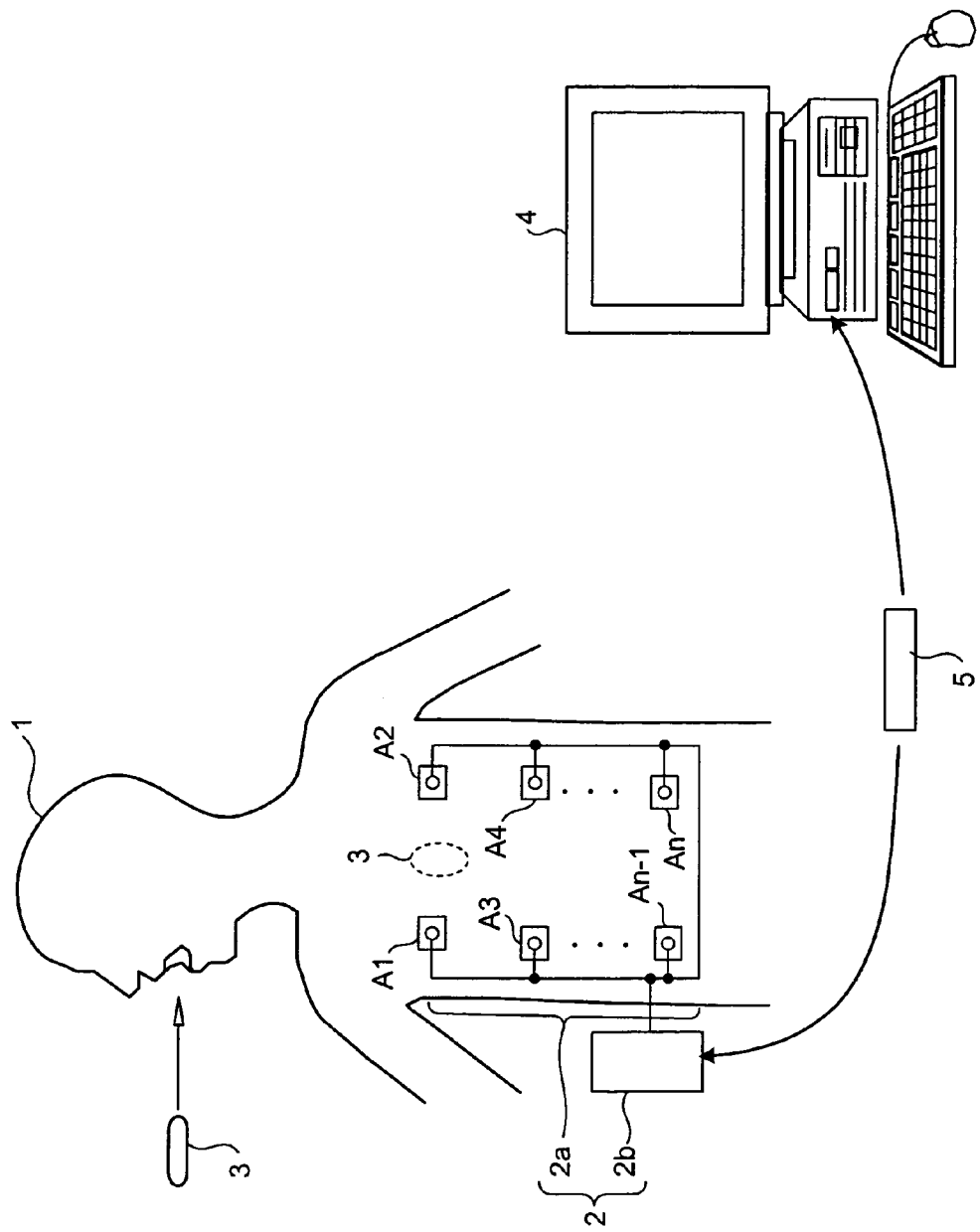
FIG. 1 is a schematic diagram showing an overall configuration of a radio in-vivo information acquiring system including a receiving device according to the present invention.

1 Subject
2 Receiving device
2a Antenna group
2b External device
3 Capsule endoscope
4 Display device
5 Portable recording medium
11 Receiving circuit
12 Signal processing circuit
13 Storage unit
14 Display unit
15 Sample-and-hold circuit
16 A/D converter
17 Power supply unit
20, 21 Holding material
A0, A01 Second outer coating (Outermost coating)
A1 to An Receiving antenna
A11 Loop unit
A12 to A82 Coaxial cable
A13 Resin plate
A14 Reinforcing plate
A15 Connecting unit cover
A16 Coaxial axis
C Control unit
C1 Selection controller
CON Connecting unit
CON1 to CONn Connector
SC Switching controller
SW Changeover switch

BEST MODE(S) FOR CARRYING OUT THE INVENTION

Exemplary embodiments of an antenna unit according to the present invention will be explained below in detail with reference to FIG. 1 to FIG. 7. Note that the present invention is not limited to the embodiments, and the embodiments can be variously modified without departing from the scope of the invention. In the embodiments below, an antenna unit that receives an image signal obtained by a capsule endoscope (a body-insertable apparatus) will be explained as one example.

First Embodiment

FIG. 1 is a schematic diagram showing an overall configuration of a radio in-vivo information acquiring system including a receiving device according to the present invention. In FIG. 1, the radio in-vivo information acquiring system includes a receiving device 2 having a radio receiving function, and a capsule endoscope 3 inserted into the inside of a subject 1. The capsule endoscope 3 images a body cavity, and performs a data transmission of an image signal to the receiving device 2. The radio in-vivo information acquiring system further includes a display device 4 that displays a body-cavity image based on the image signal received by the receiving device 2, and a portable recording medium 5 that performs a data exchange between the receiving device 2 and the display device 4. The receiving device 2 includes an antenna group 2a, and an external device 2b that processes a received radio signal. Both the antenna group 2a and the external device 20b are carried by the subject 1.

The display device 4 displays the body-cavity image or the like imaged by the capsule endoscope 3, and has a configuration like a workstation that performs an image display based on data obtained from the portable recording medium 5. More specifically, the display device 4 can be configured to display the image directly on a CRT display, a liquid crystal display, or the like, or alternatively to output the image to another medium such as a printer.

The portable recording medium 5 is attachable to and detachable from the external device 2b and the display device 4, and has a configuration so as to enable output and recording of information upon attachment to the external device 2b and the display device 4. In the embodiment, the portable recording medium 5 is attached to the external device 2b and records the data transmitted from the capsule endoscope 3 while the capsule endoscope 3 moves through the body cavity of the subject 1. After the capsule endoscope 3 is discharged from the subject 1, that is, after the capsule endoscope 3 completes the imaging the inside of the subject 1, the portable recording medium 5 is taken out from the external device 2b and attached to the display device 4. The data recorded in the portable recording medium 5 is read out by the display device 4. The data exchange between the external device 2b and the display device 4 performed by the portable recording medium 5, such as a Compact Flash (Registered Trademark) memory or the like provides a freer movement of the subject 1 while the capsule endoscope 3 images the body cavity of the subject 1, compared to the case where the data exchange is performed by a direct cable connection between the external device 2b and the display device 4. Although the portable recording medium 5 is used for the data exchange between the external device 2b and the display device 4, the present invention is not limited to such a configuration. For example, another built-in recording device such as a hard disk may be provided in the external device 2b, and the external device 2b and the display device 4 may be connected by cable or by radio for the data exchange therebetween.

Figure 2:
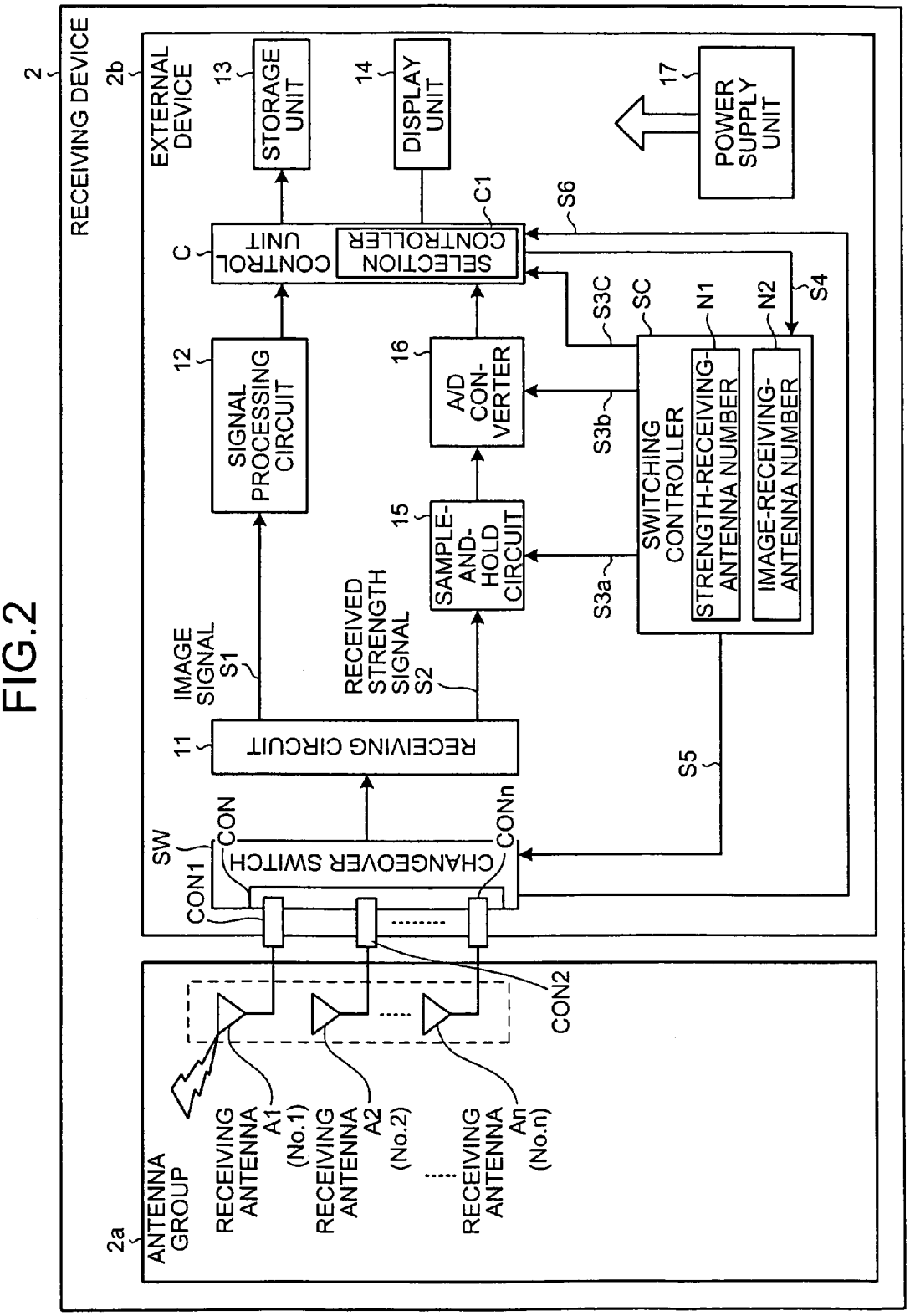
FIG. 2 is a block diagram of a configuration of the receiving device shown in FIG. 1.

The configuration of the receiving device will be explained with reference to a block diagram of FIG. 2. The receiving device 2 has a function of receiving the body-cavity image data transmitted by radio from the capsule endoscope 3. As shown in FIG. 2, the receiving device includes the antenna group 2a having receiving antennas A1 to An as an antenna unit directly applied on the external surface of the subject 1 (the body of an examinee), and the external device 2b that processes a radio signal received via the antenna group 2a. Each of the receiving antennas A1 to An can be applied on the surface of clothes such as a jacket worn by the subject 1.

On the external surface of the external device 2b, a battery pack (not shown) that accommodates a battery for power supply is attached. When the battery pack is attached to the external device 2b, the battery and internal components (described later) of the external device 2b are electrically connected. Accordingly, the power supply to these internal components is made possible. At the upper surface of the external surface of the external device 2b, there is provided a connecting unit CON for the connection of the receiving antennas A1 to An.

The external device 2b has a function of processing radio signals transmitted from the capsule endoscope 3. Specifically, the external device 2b, as shown in FIG. 2, includes a changeover switch SW that switches connections of the receiving antennas A1 to An, and a receiving circuit 11 connected at a subsequent stage of the changeover switch SW. The receiving circuit 11 amplifies and demodulates the radio signal from the receiving antennas A1 to An whose connection is switched by the changeover switch SW. The external device 2b further includes a signal processing circuit 12 and a sample-and-hold circuit 15 each at the subsequent stage of the receiving circuit 11. An A/D converter 16 is further connected at the subsequent stage of the sample-and-hold circuit 15.

A control unit C has a selection controller C1 as a control unit, and connects the signal processing circuit 12, the A/D converter 16, a storage unit 13, which corresponds to the portable recording medium 5, a display unit 14, and a switching controller SC. The switching controller SC has a strength-receiving-antenna number N1 and an image-receiving-antenna number N2, gives a switching instruction of the changeover switch SW based on these pieces of number information, and instructs a processing timing of the sample-and-hold circuit 15, the A/D converter 16, and the selection controller C1. A power supply unit 17 is made of a battery of the above battery pack, and supplies power to each of the above internal components.

The changeover switch SW of the external device 2b outputs the radio signal from the receiving antennas A1 to An to the receiving circuit 11 based on the switching instruction from the switching controller SC. The changeover switch SW has the connecting unit CON as an antenna switching unit that connects to each of the receiving antennas A1 to An at a position corresponding to an arranging position of the receiving antennas A1 to An.

The connecting unit CON has an antenna non-connection detection function (not shown) for detecting a non-connection state of each of connectors CON1 to CONn. The antenna non-connection detection function is provided to each of the connectors CON1 to CONn. The selection controller C1 detects the presence or absence of a non-connection detection signal input from the antenna non-connection detection function to determine connection states of the connectors CON1 to CONn, that is, the selection controller C1 can determine whether the receiving antennas A1 to An are connected to the external device 2b.

As explained above, the receiving circuit 11 amplifies the radio signal, outputs a demodulated image signal S1 to the signal processing circuit 12, and outputs a received strength signal S2, which indicates a received electric-field strength of the amplified radio signal, to the sample-and-hold circuit 15. The image data processed by the signal processing circuit 12 is stored in the storage unit 13 by the control unit C, and displayed and output by the display unit 14. A signal sampled and held by the sample-and-hold circuit 15 is converted into a digital signal by the A/D converter 16, and the control unit C takes in the converted digital signal. The control unit C selects a receiving antenna that has received the largest received electric-field strength as a receiving antenna of an image signal period, sequentially selects the rest of the antennas other than the selected receiving antenna as receiving antennas of a strength receiving period, and outputs to the switching controller SC the receiving antenna numbers as a signal S4 where N2 is an image-receiving-antenna number and N1 is a strength-receiving-antenna number. The selection controller C1 sets the receiving antenna as a switch-target antenna. The switch-target antennas are selected from the receiving antennas A1 to An that are actually connected, based on a signal S6. The control unit C further stores into the storage unit 13 the received electric-field strength in the strength receiving period and the received electric-field strength in the image receiving period in association with the selected receiving antenna, together with the image data. The stored received electric-field strength of each receiving antenna serves as information that calculates the position of the capsule endoscope 3 in the body cavity when the image data is received.

The switching controller SC holds the strength-receiving-antenna number N1 and the image-receiving-antenna number N2 each instructed by the selection controller C1. The switching controller SC outputs a signal S5 to the switching switch SW for instructing the switching switch SW to select and connect the receiving antennas A1 to An that correspond to the strength-receiving-antenna number N1 during the strength receiving period, and to select and connect the receiving antennas A1 to An that correspond to the image-receiving-antenna number N2 during the image receiving period. The switching controller SC outputs a signal S3a for instructing a sample-and-hold timing by the sample-and-hold circuit 15, a signal S3b for instructing an A/D conversion timing by the A/D converter 16, and a signal S3c for instructing a selection control timing by the selection controller C1.

Figure 3:
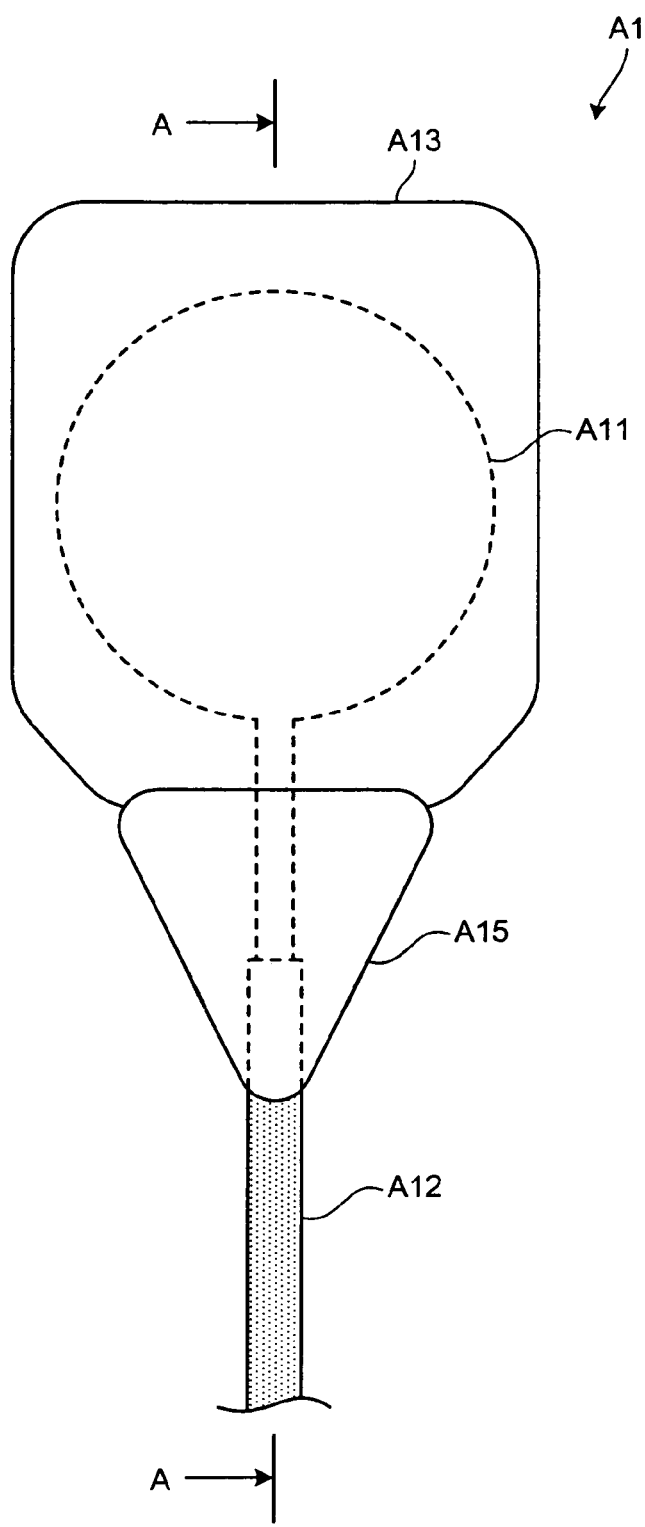
FIG. 3 is a schematic diagram of an example of a configuration of the receiving antenna shown in FIG. 2.
Figure 4:
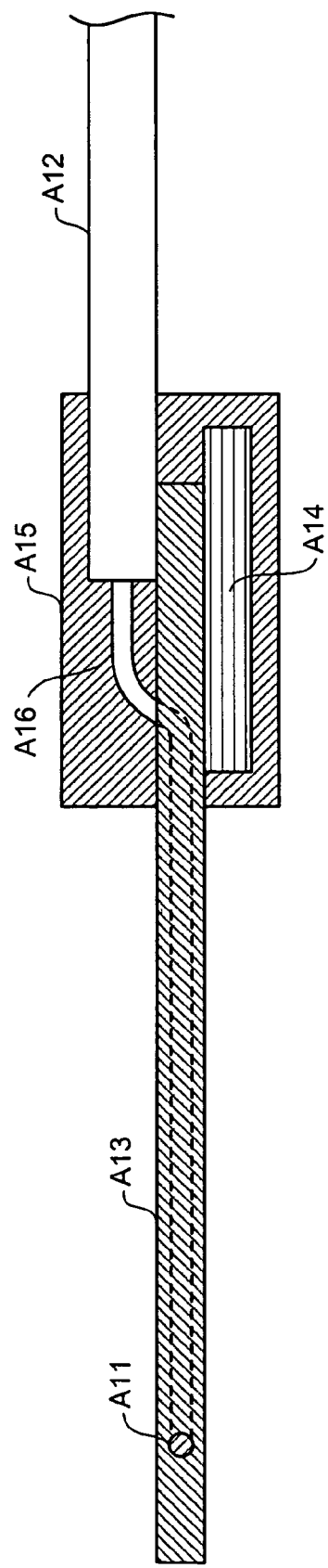
FIG. 4 is a cross-sectional view taken along the line A-A in FIG. 3.

The receiving antennas A1 to An that forms part of the antenna unit have the connectors CON1 to CONn that connect to the connecting unit CON described above. These receiving antennas A1 to An each employ the same configuration. The configuration of the receiving antenna A1 is shown in FIG. 3 and FIG. 4 as an example that represents the receiving antennas A1 to An. FIG. 3 is a schematic diagram of an example of a configuration of the receiving antenna shown in FIG. 2. FIG. 4 is a cross-sectional view taken along the line A-A of FIG. 3. In FIG. 3 and FIG. 4, the receiving antenna A1 is formed of a loop antenna, for example. The receiving antenna A1 includes: a loop unit A11 formed in a loop shape and having an end, which is an antenna main body; a coaxial cable A12 of which one end is attached to the end of the loop unit A11 and the other end is attached to the connector CON1; a resin plate A13, which serves as an antenna coating member, that envelopes at least one portion of the loop unit A11 (in this embodiment, the loop unit A11 is completely buried inside); a reinforcing plate A14 that reinforces the resin plate A13 from below of FIG. 4; and a connecting unit cover A15 that covers a portion where the loop unit A11 and the coaxial cable A12 are electrically connected. The loop unit A11 and the resin plate A13 configure the antenna according to the present invention.

The resin plate A13 is made of a resin member in an approximate rectangular shape of which four corners are beveled, for example, made of a material such as polyimide. The resin plate A13 holds the buried loop unit A11 so that a deformation and disconnecting of the loop unit A11 are prevented. The connecting unit cover A15 is made of a resin member in an approximate triangular shape of which three corners are beveled, for example. The connecting unit cover A15 is formed so as to cover the end of the loop unit A11 and a connecting portion of the coaxial cable A12. The fusing point of the connecting unit cover A15 is rendered approximately the same as that of the resin plate A13 or that of the outer coating (the outermost layer) of the coaxial cable A12. The reason for this is to improve drip-proofness at the time of fusing the connecting unit cover A15 with the resin plate A13 or with the coaxial cable A12. The connecting unit cover A15 is configured to be made of a resin member, that is, a material such as polyimide, which is the same material as that of the resin plate A13, or polyethylene, which is the same material as that of the outer coating of the coaxial cable. The connecting unit cover A15 has compatibility with the resin plate A13 or the outer coating of the coaxial cable A12 at the time of fusing with the resin plate A13 or the coaxial cable A12 by thermal treatment.

In this case, the fusing means adhesion that is performed as follows: all of or one portion of two members are brought into a liquid state by raising a temperature up to the fusing point or higher, and the two members are contacted, and thereafter, the two members are cooled. The compatibility means a state of being mixed in which at least two substances have affinity, and are mixed and not separated when the substances are in a liquid state.

In this embodiment, the addition of temperatures up to the fusing point or higher by heat treatment, for example, to the connecting unit cover A15, the resin plate A13, and the outer coating of the coaxial cable A12 leads to the fusing of the connecting unit cover A15 with the resin plate A13 and the coaxial cable A12. This results in a favorable bonding of the connecting unit cover A15 with the coaxial cable A12 or with the resin plate A13.

That is, in manufacturing an antenna unit by heat treatment, for example, following steps are performed. Firstly, in a connection step, the antenna composed of the loop unit A11 and the resin plate A13, and the coaxial cable A12 are electrically connected by soldering, for example. In a subsequent frame-fitting step, the antenna and the coaxial cable A12 electrically connected are fitted into a mold. In a material charging step that follows, a liquefied material that configures the connecting unit cover A15 is charged so that the outermost layer of the coaxial cable A12 melts and the liquefied material that configures the connecting unit cover A15 is charged so as to be compatible with a material that configures the outermost layer of the coaxial cable A12. In a subsequent cooling step, the resultant antenna unit is cooled so that the connecting unit cover A15 and the coaxial cable A12 are joined, whereby a gap that exists between the connecting unit cover A15 and the coaxial cable A12 is sealed. Accordingly, water is prevented from entering.

In this manner, in this embodiment, the coaxial cable and the connecting unit cover configured of a material having approximately the same fusing point are fused by heat treatment, so that a gap that exists between the coaxial cable and the connecting unit cover is sealed, whereby drip-proofness between the connecting unit cover and the antenna is enhanced. As a result, when disinfectant is sprayed by misting, for example, it becomes possible to prevent water from entering from the above gap into an electrical connecting unit that resides inside the connecting unit cover.

In the present invention, at the time of fusing the connecting unit cover and the coaxial cable, and fusing the connecting unit cover and the resin plate, when the connecting unit cover and the outer coating of the coaxial cable are configured of the same material, the connecting unit cover and the resin plate are configured of at least one of a material having approximately the same fusing point and a material having compatibility. Alternatively, when the connecting unit cover and the resin plate are configured of the same material, the connecting unit cover and the outer coating of the coaxial cable are configured of at least one of a material having approximately the same fusing point and a material having compatibility. In these cases, it is possible to fuse by heat treatment the antenna and the connecting unit cover, and fuse the connecting unit cover and the coaxial cable. This provides a more secured way to prevent water from entering not only the connecting unit, but also inside the antenna, thereby further improving the drip-proofness of the antenna unit. In the present invention, the effect similar to the above can be obtained also when the connecting unit cover, the coaxial cable, and the resin plate are configured of a material having approximately the same fusing point or a material having compatibility.

In the present invention, it is needless to mention that the material of the connecting unit cover A15 includes not only the above mentioned materials such as polyimide and polyethylene, but also other materials such as polyurethane that are fused with the outer coating of the coaxial cable A12 or the resin plate A13, or a material having compatibility with these components at the time of the heat treatment.

Second Embodiment

The processing for sealing the gap that exists at the connecting unit cover with the coaxial cable and the resin plate shown in FIG. 3 and FIG. 4 is not only limited to the above heat treatment, but also includes bonding by thermocompression bonding processing, for example, for sealing the above gap. Also in this case also, the connecting unit cover A15 is configured to be made of a resin member, which is the same member as the resin plate A13 or the outer coating of the coaxial cable, for example, for enhancing adhesiveness and drip-proofness with the resin plate A13 or the coaxial cable A12.

In this embodiment, the connecting unit cover A15 is applied a pressure at a predetermined temperature by thermocompression bonding, for example. As a result, plastic deformation occurs in the connecting unit cover A15, whereby the outer coating of the coaxial cable A12 and the resin plate A13 of the antenna are bonded. Consequently, it becomes possible to join the connecting unit cover A15 with the coaxial cable A12 in a favorable manner, and the resin plate A13 in a die forming step in which the connecting unit is pressed. It becomes also possible to prevent adverse effects such as melting of the outer coating caused due to a difference in curing temperature.

Thus, in this embodiment, the antenna, the coaxial cable, and the connecting unit configured of a material having thermal-adhesiveness are bonded by thermocompression bonding, whereby a gap between materials is eliminated. Accordingly, adhesiveness of the connecting unit cover with the antenna and the coaxial cable is enhanced. Therefore, it becomes possible to prevent water from entering the interior of the connecting unit when disinfectant is sprayed by misting, for example. Thereby, the drip-proofness of the antenna unit can be improved.

In this embodiment, a connecting unit cover having high drip-proofness is bonded to the connecting unit of the antenna unit by thermocompression bonding, so that it becomes possible to surely prevent water from entering not only the connecting unit, but also the interior of the antenna. It becomes also possible to improve the drip-proofness of the antenna unit.

In the present invention, it is needless to mention that the material of the connecting unit cover A15 includes not only the above mentioned materials such as polyimide and polyethylene, but also other materials such as polyurethane bonded to the resin plate A13 or the outer coating of the coaxial cable A12 at the time of the application of a pressure at a predetermined temperature by thermocompression bonding, for example.

In the present invention, in addition to the above thermocompression bonding, the application of external force to the connecting unit cover allows the connecting unit cover A15 to adhere to the resin plate A13 and the coaxial cable A12, similar to the case of this embodiment. In the case of a step in which the external force is applied, when a material having force brought about from the interior of the material generated by applied external force being approximately equal to that of the resin plate A13 and the outer coating of the coaxial cable A12 is used, the adhesiveness can be improved.

Third Embodiment

Figure 5:
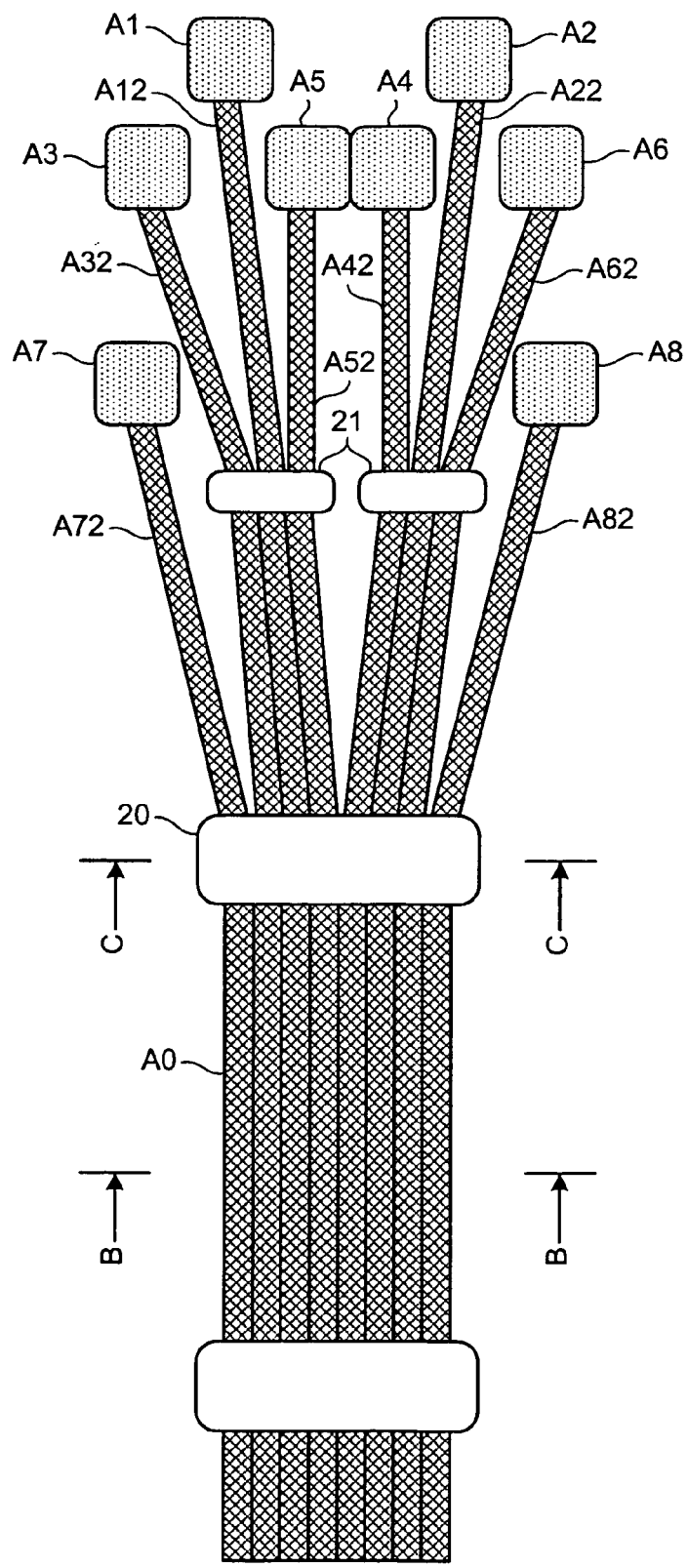
FIG. 5 is a schematic diagram showing a configuration of an antenna group shown in FIG. 1.

The configuration of coaxial cables A12 to An2 of each of receiving antennas A1 to An according to a third embodiment will be explained based on FIG. 5 to FIG. 7. Of these drawings, FIG. 5 is a configuration diagram showing a configuration of an antenna group, FIG. 6 is a cross-sectional view taken along the line B-B in FIG. 5, FIG. 7 is a cross-sectional view taken along the line C-C in FIG. 5. Note that, in this embodiment, a case where eight coaxial cables A12 to A82, for example, are formed as one unit will be explained. In FIG. 6 and FIG. 7, the coaxial cables A42 to A72 that are present in the antenna group are omitted for the sake of illustration.

Generally, a coaxial cable is configured of a four-layered structure, including a coaxial axis provided in the center, an insulator so as to cover the coaxial axis, a shield, and an outer coating. The outer coating is formed of the polyethylene described above. In contrast, as shown in FIG. 5 and FIG. 6, an antenna group 2a according to the present invention is formed of a five-layered structure in which a plurality of four-layered structured coaxial cables, that is, in this embodiment, eight coaxial cables A12 to A82, for example, are aligned horizontally (in the right and left directions) of FIG. 6 with predetermined intervals provided therebetween, and the coaxial cables A12 to A82 are coated by a second outer coating (the outermost coating) A0 so as to cover the outer coatings (hereinafter, "intermediate coating layers") of these coaxial cables A12 to A82. The outermost layer A0 is configured to couple each of the coaxial cables A12 to A82 so that the coaxial cables A12 to A82 become a flat cable in one unit. Coating processing of the outermost layer A0 of the coaxial cable A12 can be performed by fusing through thermal treatment processing as shown in the first embodiment, and also can be performed by thermal bonding through die forming processing as shown in the second embodiment.

In the electrical connecting unit between the antenna and the coaxial cable, a coaxial axis A16 exposed from the intermediate coating layer and the outermost layer of the coaxial cable A12 is electrically connected to the loop unit A11 of the antenna, and the coaxial cable A12 is fused to the connecting unit cover A15, whereby they are integrally configured, as shown in FIG. 4.

The end of the coaxial cable on the side of the receiving device 2 advances in the interior of the external device 2b of the receiving device 2, and connected to the connecting unit CON of the external device 2b via the connectors CON1 to CONn shown in FIG. 2. The outermost layer A0 of the coaxial cable A12 is provided such that the outermost layer A0 advances at least to the interior of the external device 2b.

Thus, in this embodiment, all of the coaxial cable and the connecting unit are coated with the outermost layer, so that a gap between each material is eliminated, whereby connectivity between the coaxial cable and the outermost layer is enhanced. Accordingly, it becomes possible to prevent water from entering the interior of the connecting unit when disinfectant is sprayed by misting, for example, and the drip-proofness of the antenna unit is thereby improved.

In this embodiment, the outermost layer of the coaxial cable is provided so as to advance at least to the interior of the receiving device, so that it becomes possible to prevent water from entering the gap that exists at the connecting unit between the coaxial cable and the receiving device when disinfectant is sprayed by misting, for example. Accordingly, the drip-proofness of the receiving device can also be improved.

In this embodiment, the coaxial cables are aligned horizontally and coupled at the outermost layer level, so that the coaxial cables become flat. Accordingly, it becomes easy to handle a plurality of cables, and movability in the vertical direction (in the up and down directions) of FIG. 6 is not inhibited, thereby an attaching work becomes easy at the time of attaching the antenna element on the external surface of a subject.

In the present invention, it is needless to mention that the material of the outermost layer A0 includes not only the above mentioned material such as polyurethane, but also other materials such as polyurethane that has adhesiveness and has the same stress as that of the outer layer of the coaxial cable at the time of the application of external force by thermocompression bonding, for example. In this embodiment, although the coaxial cables are aligned horizontally, these cables can be aligned in a plurality of lines when movability is taken into consideration.

In the present invention, in addition to the thermocompression bonding described above, also when the external force is applied to the outermost layer, the coaxial cable and the outermost layer can be bonded as in the case of this embodiment. When working processing in which the external force is applied is used, a material having force brought about by the applied external force being approximately the same as that of a material for the coaxial cable is used as the material for the outermost layer, whereby adhesiveness can be enhanced.

Fourth Embodiment

As shown in FIG. 5, each of the coaxial cables A12 to A82 is-set such that the length thereof appropriately corresponds to each position attached to the subject 1. In order to enable the attaching, the outermost layer A01 in a gap is cut along the longitudinal direction of the cable, so that each of the coaxial cables A12 to A82, which are on the antenna main body side, is set to the appropriate length. The above connection between the antenna main body and the coaxial cable is performed after the outermost layer A0 is formed on the coaxial cable and each coaxial cable is set to the appropriate length.

Thus, in this embodiment, the gap between the coaxial cables is cut so that each coaxial cable is set to an appropriate length. Therefore, when the coaxial cable is used as it is, the cutting between the coaxial cables is probably made longer during its use, and the coaxial cables come into a free operative state, resulting in becoming tangled. Therefore, in this embodiment, for preventing the tangling, there is provided a holding material 20 that holds each coaxial cable from above the outermost layer A0 and maintains a state where the coaxial cables A12 to A82 are aligned horizontally.

The holding material 20 is formed in an approximate rectangular shape. As shown in FIG. 7, the holding material 20 covers the outermost layer A0 formed on the external surface of the coaxial cables A12 to A82, and is formed so that the gap is filled. Thus, the holding material 20 can prevent the cutting from occurring in the outermost layer A01 in the gap during its use, for example.

The holding material 20 is preferably configured of the same material as the outermost layer A0 for fusing with the outermost layer A0 by thermal treatment, for example. With this arrangement, in this embodiment, the coaxial cable at a predetermined position is fitted into a mold. A liquefied material that configures the holding material 20 is charged into the mold so that the outermost layer A0 of the coaxial cable melts and a liquefied material that configures the holding material 20 becomes compatible with a material that configures the outermost layer A0. Thereafter, the melt is cooled, whereby the holding material 20 is joined to the coaxial cable.

Thus, in this embodiment, the holding material and each coaxial cable are fused, and a state where each coaxial cable is aligned horizontally is maintained by a holding element, so that it is possible to prevent the cutting from occurring in the gap between the coaxial cables during its use. Therefore, it is possible to set each coaxial cable to the appropriate length. This makes it possible to prevent the coaxial cables from being tangled, for example.

It should be understood that, in this embodiment, the case where the holding material 20 that holds eight coaxial cables A12 to A82 is explained, but the present invention is not limited thereto. For example, as shown in FIG. 5, it is possible to prevent the cutting from occurring in the gap between the coaxial cables by using a small holding material 21 when adjacent coaxial cables, that is, coaxial cables A12, A32, A52, and coaxial cable A22, A42, A62 in this embodiment, are held in a horizontally aligned state, whereby it becomes possible to hold the coaxial cables at a thinner portion, and also possible to set each coaxial cable to the appropriate length. It is needless to mention that, also when the holding member having drip-proofness is used, it is possible to enhance adhesiveness with the outermost layer by thermocompression bonding or processing for applying external force, similar to the case of the connecting unit cover and the outermost layer described above.

With such a configuration, in this embodiment, the antenna and the coaxial cable can be covered in a seamless manner by the connecting unit cover and the outermost layer, so that it is possible to prevent water from entering from the gap when disinfectant is sprayed by misting, for example, and thus, the drip-proofness of the antenna unit can be improved. At the same time, it is possible to improve user friendliness of the antenna unit by using the holding material.

Note that while the case of the antenna unit has been explained in this embodiment, the present invention is not limited thereto. As long as the coaxial cable is used, the present invention is applicable. For example, when a device that requires drip-proofness and a coaxial cable are connected, the forming of a connecting unit that connects the device and the coaxial cable, for example, a connector unit and the coaxial cable as in the case of the embodiment, can similarly improve the drip-proofness. In this embodiment, while the case where a plurality of coaxial cables are used has been explained, it is needless to mention that the present invention is applicable to a case where one cable is used.

INDUSTRIAL APPLICABILITY

In this manner, an antenna unit and a method of manufacturing an antenna unit according to the present invention is effective for a medical observation apparatus that observes a subject region. Particularly, the present invention is suitable for prevention of water from entering a gap that exists at a connecting unit between an antenna of an antenna unit and a coaxial cable, whereby the drip-proofness is improved.

The invention claimed is:

1. An antenna unit, comprising:
   an antenna attached to a body of an examinee;
   a coaxial cable that can transmit a signal received by the antenna to a receiving device;
   a connecting unit cover that covers an electrical connecting unit between the antenna and the coaxial cable, wherein
   a fusing point of an outermost layer of the coaxial cable and a fusing point of the connecting unit cover are made approximately the same, and the coaxial cable and the connecting unit cover are fused.

2. The antenna unit according to claim 1, wherein the outermost layer of the coaxial cable and the connecting unit cover have compatibility at the time of fusing the outermost layer of the coaxial cable and the connecting unit cover.

3. The antenna unit according to claim 1, wherein the outermost layer of the coaxial cable and the connecting unit cover are formed of the same material.

4. The antenna unit according to claim 1, wherein the antenna includes:
   an antenna main body; and
   an antenna coating member that envelopes the antenna main body into an interior of the antenna coating member, wherein
   the antenna coating member is formed of a material having compatibility with the connecting unit cover at the time of fusing the antenna coating member with the connecting unit cover.

5. The antenna unit according to claim 1, wherein the coaxial cable is formed such that the outermost layer covers an intermediate coating layer formed of polyethylene.

6. The antenna unit according to claim 5, wherein the electrical connecting unit is formed such that coaxial axis exposed from the intermediate coating layer and the outermost layer of the coaxial cable is connected to the antenna.

7. The antenna unit according to claim 1, wherein the coaxial cable enters into an interior of the receiving device so that the coaxial cable and the receiving device are connected, and the outermost layer is provided such that the outermost layer advances at least to the interior of the receiving device.

8. A method for manufacturing an antenna unit, comprising:
   fitting a coaxial cable and an antenna electrically connected into a mold;
   charging into the mold a liquefied material that configures a connecting unit cover that covers an electrical connecting unit between the antenna and the coaxial cable so that an outermost layer of the coaxial cable melts and the liquefied material that configures the connecting unit cover is compatible with a material that configures the outermost layer; and
   connecting the connecting unit cover to the coaxial cable after cooling.

* * * * *